United States Patent
Cheng et al.

(10) Patent No.: US 8,052,894 B2
(45) Date of Patent: Nov. 8, 2011

(54) SALICYLATE SUBSTITUTED CONJUGATED POLYMERS AND DEVICES

(75) Inventors: Yang Cheng, Midland, MI (US); Michael Inbasekaran, Midland, MI (US); Chun Wang, Midland, MI (US)

(73) Assignee: Sumitomo Chemical Company, Limited, Tokyo (JP)

( * ) Notice: Subject to any disclaimer, the term of this patent is extended or adjusted under 35 U.S.C. 154(b) by 805 days.

(21) Appl. No.: 11/577,430

(22) PCT Filed: Dec. 1, 2005

(86) PCT No.: PCT/US2005/043225
§ 371 (c)(1),
(2), (4) Date: Apr. 23, 2008

(87) PCT Pub. No.: WO2006/060437
PCT Pub. Date: Jun. 8, 2006

(65) Prior Publication Data
US 2009/0001324 A1    Jan. 1, 2009

Related U.S. Application Data

(60) Provisional application No. 60/633,356, filed on Dec. 3, 2004.

(51) Int. Cl.
*H01B 1/12* (2006.01)
*C07C 69/753* (2006.01)
*C08G 63/18* (2006.01)

(52) U.S. Cl. ............... 252/500; 528/298; 560/121

(58) Field of Classification Search .............. 252/500; 528/298; 560/121
See application file for complete search history.

(56) References Cited

U.S. PATENT DOCUMENTS

| | | | |
|---|---|---|---|
| 2010/0001263 A1* | 1/2010 | Noguchi et al. | 257/40 |
| 2010/0033085 A1* | 2/2010 | Nakatani et al. | 313/504 |
| 2010/0090206 A1* | 4/2010 | Nakatani et al. | 257/40 |
| 2010/0176377 A1* | 7/2010 | Fukushima et al. | 257/40 |

FOREIGN PATENT DOCUMENTS

WO   WO 2005/049548 A1    6/2005

* cited by examiner

*Primary Examiner* — Joseph Kosack
(74) *Attorney, Agent, or Firm* — Sughrue Mion, PLLC

(57) ABSTRACT

A compound having a structural unit of Formula: (I). A polymer having a structural unit of Formula: (II). A conjugated polymer having one or more side groups of the following Formula: (III). Additionally, compositions, polymer blends, films, coatings, and electronic devices prepared from such polymers.

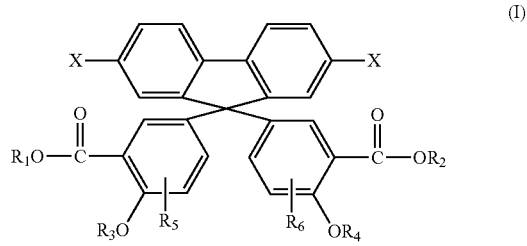

(I)

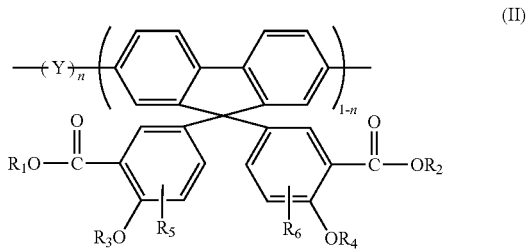

(II)

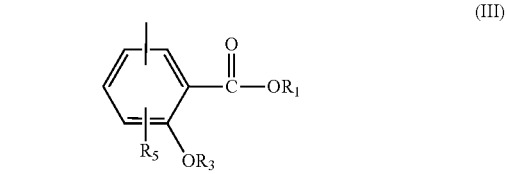

(III)

12 Claims, No Drawings

SALICYLATE SUBSTITUTED CONJUGATED POLYMERS AND DEVICES

This application claims the benefit of the provisional application, U.S. Application No. 60/633,356, filed Dec. 3, 2004, which is incorporated herein by reference.

BACKGROUND

This invention relates to salicylate substituted monomers such as salicylate substituted fluorene monomers and conjugated polymers having salicylate side groups. The invention also relates to compositions, films and coatings prepared from such polymers as well as electronic devices comprising such polymers.

Various substituted fluorene containing polymers have been discovered which are useful in optoelectronic devices such as light emitting diodes, transistors and photocells, see, for example, U.S. Pat. Nos. 6,605,373; 6,593,450; 6,514,632; 6,512,083; 6,383,664; 6,353,083; 6,309,763; 6,255,449; 6,255,447; 6,204,515; 6,169,163; 5,962,631 and 5,708,130, each of which are herein fully incorporated by reference. Despite the outstanding success of such and other conjugated polymers and the devices made therefrom, it would be a further advance in the art if conjugated polymers were discovered that increased the efficiency and lifetime characteristics of devices made therefrom.

SUMMARY OF THE INVENTION

The instant invention comprises a conjugated polymer that provides increased efficiency and lifetime characteristics of devices made therefrom. In one embodiment the instant invention is a conjugated polymer comprising a side group of the following formula (III) in which $R_1$ and $R_3$, are the same or different and each is independently H, alkyl in which one or more C and/or H may be substituted by any hetero atom, such as O, N, S, Si, P and F, aralkyl, aryl, substituted aryl, heteroaryl, or substituted heteroaryl. $R_5$ is hydrogen, $C_{1-20}$ hydrocarbyl, $C_{1-20}$ hydrocarbyloxy, $C_{1-20}$ thioether, $C_{1-20}$ hydrocarbyloxycarbonyl, $C_{1-20}$ hydrocarbylcarbonyloxy, cyano, or fluoro.

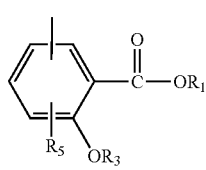

Formula (III)

In another embodiment, the instant invention is a polymer comprising a structure unit of the following formula (II) in which $R_1$, $R_2$, $R_3$, $R_4$ are the same or different and each is independently H; alkyl in which one or more C and/or H may be substituted by any hetero atom, such as O, N, S, Si, P and F, aralkyl, aryl, substituted aryl, heteroaryl, or substituted heteroaryl; and Y is a conjugated unit; and $R_5$ and $R_6$ are the same or different and each is independently in each occurrence hydrogen, $C_{1-20}$ hydrocarbyl, $C_{1-20}$ hydrocarbyloxy, $C_{1-20}$ thioether, $C_{1-20}$ hydrocarbyloxycarbonyl, $C_{1-20}$ hydrocarbylcarbonyloxy, cyano, or fluoro; n is a real number ranging from at or between 0 to 0.999.

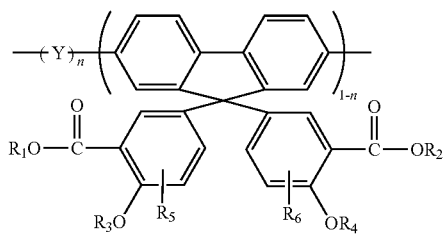

Formula (II)

In another embodiment, the instant invention is a compound having the following formula (I) in which $R_1$, $R_2$, $R_3$, $R_4$ are the same or different and each is independently H, alkyl in which one or more C and/or H may be substituted by any hetero atom, such as O, N, S, Si, P and F, aralkyl, aryl, substituted aryl, heteroaryl, substituted heteroaryl; X is any halogen, boronic acid or boronate ester; and $R_5$ and $R_6$ are the same or different and each is independently in each occurrence hydrogen, $C_{1-20}$ hydrocarbyl, $C_{1-20}$ hydrocarbyloxy, $C_{1-20}$ thioether, $C_{1-20}$ hydrocarbyloxycarbonyl, $C_{1-20}$ hydrocarbylcarbonyloxy, cyano, or fluoro.

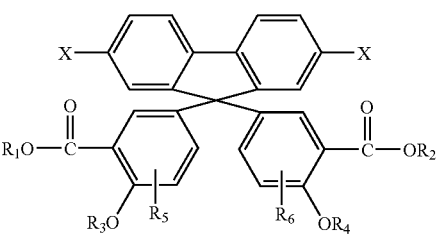

Formula (I)

DETAILED DESCRIPTION OF THE INVENTION

In one embodiment, the instant invention is a compound having Formula (I) in which $R_1$, $R_2$, $R_3$, $R_4$ are the same or different and each is independently H; alkyl in which one or more C and/or H is substituted by any hetero atom, such as O, N, S, Si, P and F, aralkyl, aryl, substituted aryl, heteroaryl, substituted heteroaryl; X is any halogen, boronic acid or boronate ester; and $R_5$ and $R_6$ are the same or different and each is independently in each occurrence hydrogen, $C_{1-20}$ hydrocarbyl, $C_{1-20}$ hydrocarbyloxy, thioether, $C_{1-20}$ hydrocarbyloxycarbonyl, $C_{1-20}$ hydrocarbylcarbonyloxy, cyano, or fluoro.

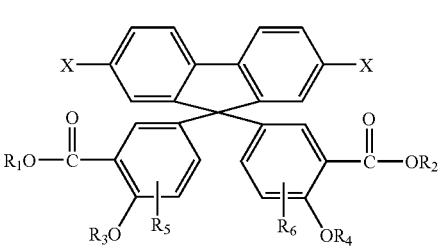

Formula (I)

The compound having Formula (I) can be made using the procedure detailed in the above cited patents.

In another embodiment the instant invention is a polymer comprising a structure unit of Formula (II) in which $R_1$, $R_2$, R$_3$, R$_4$ are the same or different and each is independently H, alkyl in which one or more C and/or H may be substituted by any hetero atom, such as O, N, S, Si, P and F, aralkyl, aryl, substituted aryl, heteroaryl, substituted heteroaryl; and Y is any conjugated unit; and R$_5$ and R$_6$ are the same or different and each is independently in each occurrence hydrogen, C$_{1-20}$ hydrocarbyl, C$_{1-20}$ hydrocarbyloxy, C$_{1-20}$ thioether, C$_{1-20}$ hydrocarbyloxycarbonyl, C$_{1-20}$ hydrocarbylcarbonyloxy, cyano, or fluoro; n is a real number ranging from at or between 0 to 0.999.

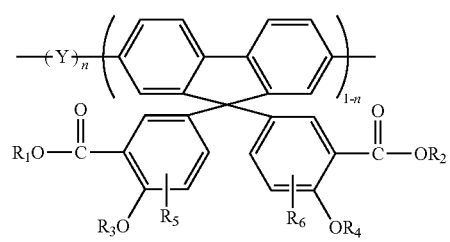

Formula (II)

In Formula (II), n may be zero and the Y moiety may be absent. If n is not zero then the Y moiety in Formula (II) can be one or more of the following moieties:

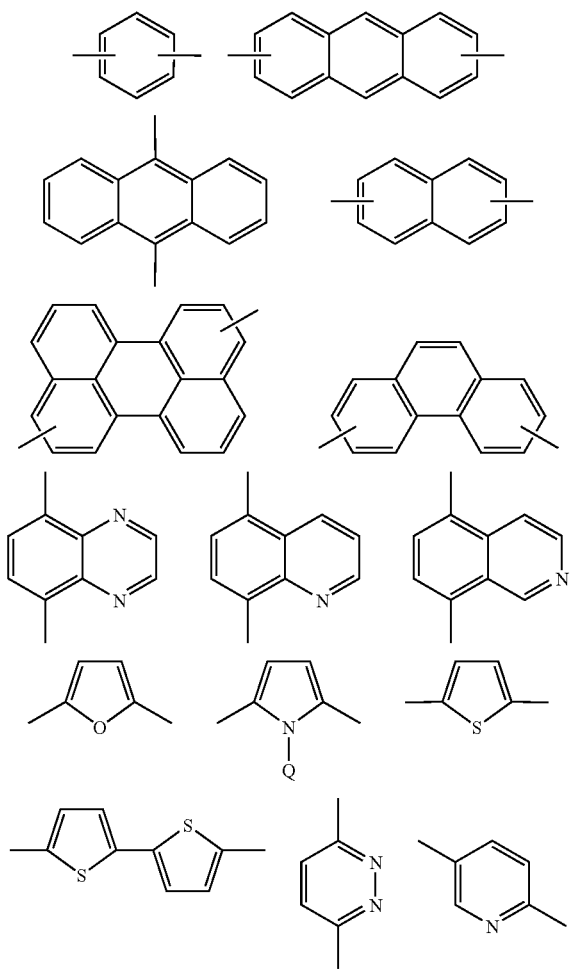

-continued

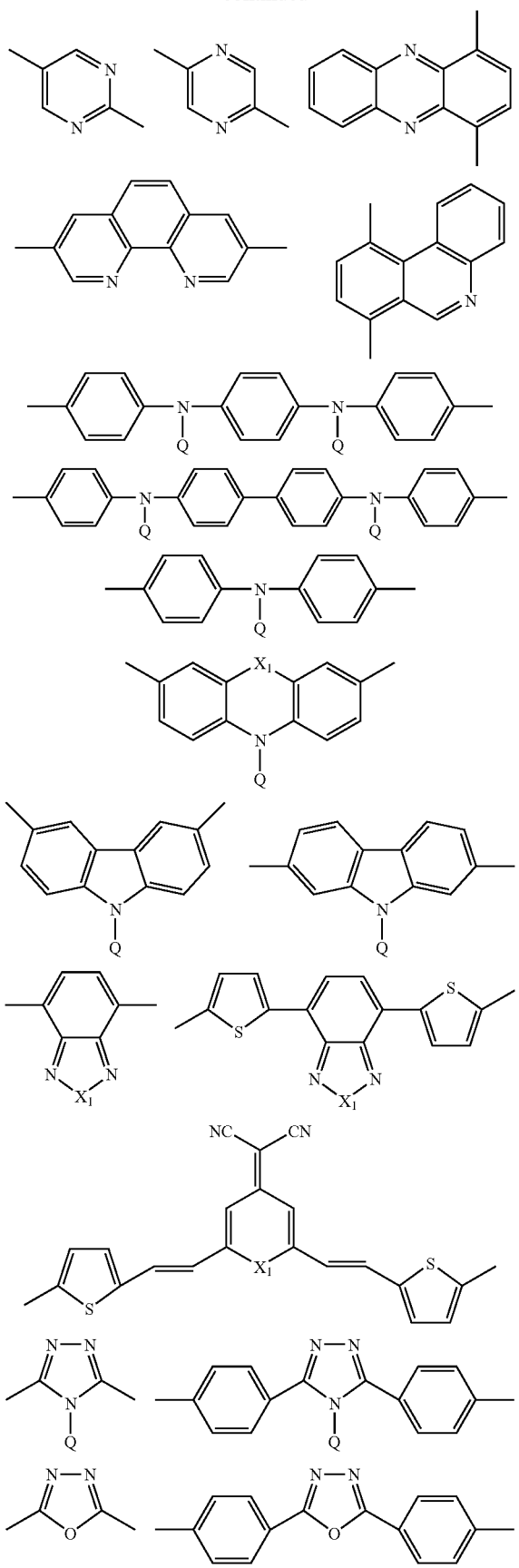

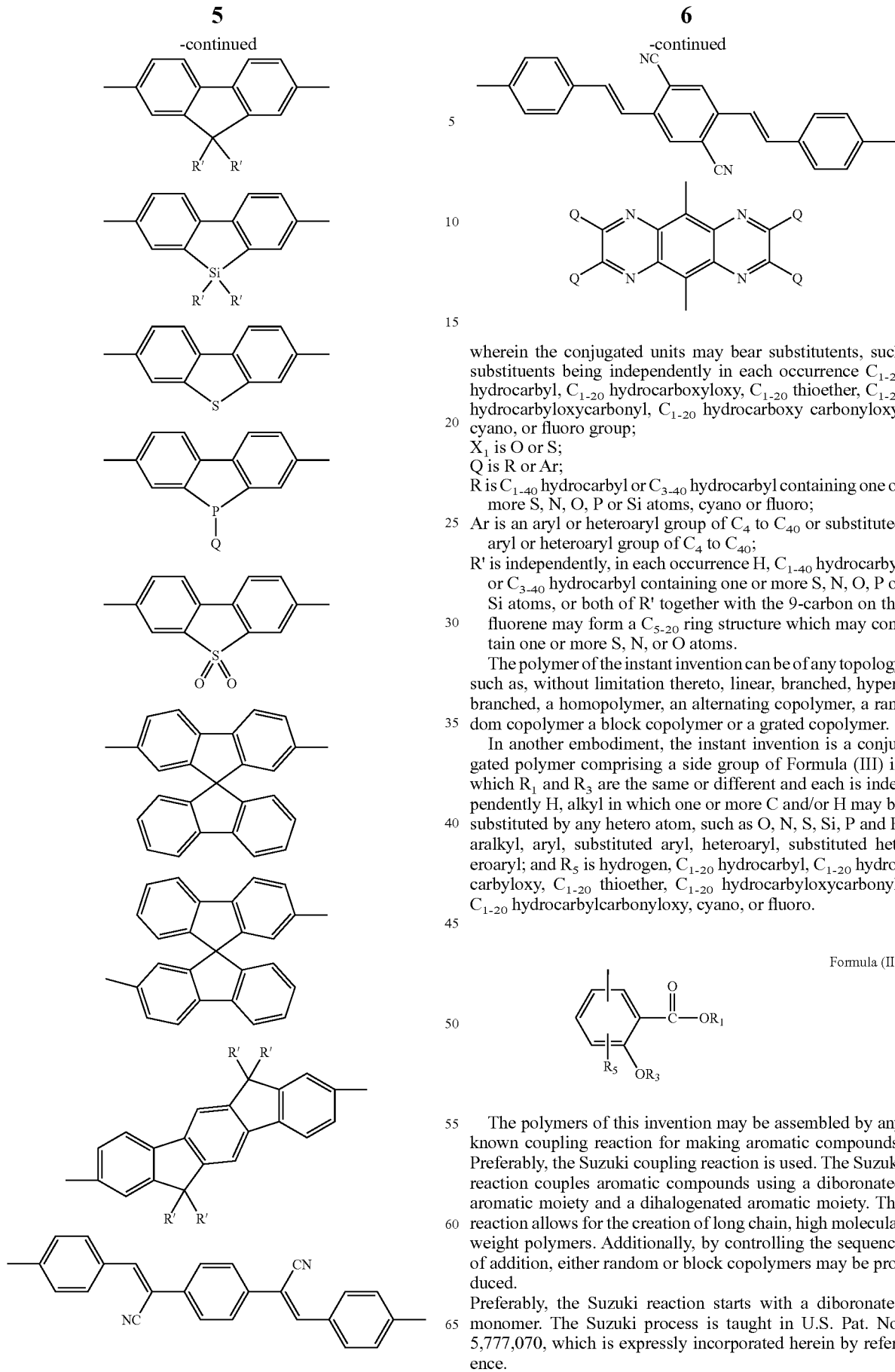

wherein the conjugated units may bear substitutents, such substituents being independently in each occurrence $C_{1-20}$ hydrocarbyl, $C_{1-20}$ hydrocarboxyloxy, $C_{1-20}$ thioether, $C_{1-20}$ hydrocarbyloxycarbonyl, $C_{1-20}$ hydrocarboxy carbonyloxy, cyano, or fluoro group;

$X_1$ is O or S;

Q is R or Ar;

R is $C_{1-40}$ hydrocarbyl or $C_{3-40}$ hydrocarbyl containing one or more S, N, O, P or Si atoms, cyano or fluoro;

Ar is an aryl or heteroaryl group of $C_4$ to $C_{40}$ or substituted aryl or heteroaryl group of $C_4$ to $C_{40}$;

R' is independently, in each occurrence H, $C_{1-40}$ hydrocarbyl or $C_{3-40}$ hydrocarbyl containing one or more S, N, O, P or Si atoms, or both of R' together with the 9-carbon on the fluorene may form a $C_{5-20}$ ring structure which may contain one or more S, N, or O atoms.

The polymer of the instant invention can be of any topology such as, without limitation thereto, linear, branched, hyperbranched, a homopolymer, an alternating copolymer, a random copolymer a block copolymer or a grated copolymer.

In another embodiment, the instant invention is a conjugated polymer comprising a side group of Formula (III) in which $R_1$ and $R_3$ are the same or different and each is independently H, alkyl in which one or more C and/or H may be substituted by any hetero atom, such as O, N, S, Si, P and F, aralkyl, aryl, substituted aryl, heteroaryl, substituted heteroaryl; and $R_5$ is hydrogen, $C_{1-20}$ hydrocarbyl, $C_{1-20}$ hydrocarbyloxy, $C_{1-20}$ thioether, $C_{1-20}$ hydrocarbyloxycarbonyl, $C_{1-20}$ hydrocarbylcarbonyloxy, cyano, or fluoro.

Formula (III)

The polymers of this invention may be assembled by any known coupling reaction for making aromatic compounds. Preferably, the Suzuki coupling reaction is used. The Suzuki reaction couples aromatic compounds using a diboronated aromatic moiety and a dihalogenated aromatic moiety. The reaction allows for the creation of long chain, high molecular weight polymers. Additionally, by controlling the sequence of addition, either random or block copolymers may be produced.

Preferably, the Suzuki reaction starts with a diboronated monomer. The Suzuki process is taught in U.S. Pat. No. 5,777,070, which is expressly incorporated herein by reference.

The polymers of the invention preferably have a weight average molecular weight of about 10,000 Daltons or greater, 20,000 Daltons or greater, or preferably 50,000 Daltons or greater; 1,000,000 Daltons or less, 500,000 Daltons or less, or preferably 400,000 Daltons or less. Molecular weights are determined using gel permeation chromatography using polystyrene as an internal standard.

Another embodiment of this invention is related to polymer blends. The blends comprise a polymer comprising repeat units of Formula (II) or a polymer having the side group of Formula (III) blended with at least one other conjugated polymer. As used herein, the term "conjugated polymer" means a polymer with a backbone of overlapping π orbitals. Conjugated polymers that may be used in the blends include polyfluorenes, poly(arylenevinylene), polyphenylenes, poly-indenofluorenes and polythiophenes, including homopolymers, co-polymers or substituted homopolymers and/or copolymers of any of these conjugated polymers.

Preferably the polymer blend is composed of at least 1 weight percent of a polymer comprising units of Formula II or having the side groups of Formula III. Preferably the band gap of the conjugated polymer is narrower than the band gap of polymer containing units of Formula II. Preferred polymer blends have high photoluminescent and electroluminescent efficiency. Other additives such as viscosity modifiers, anti-oxidants and coating improvers may optionally be added. Additionally, blends of two or more low polydispersity polymers of similar compositions but different molecular weight can also be formulated. Preferably, the polymers demonstrate a polydispersity (Mw/Mn) of 10 or less, more preferably 5 or less, even more preferably 4 or less and most preferably 3 or less.

Another embodiment of this invention is the films formed from the polymers of the invention. Such films can be used in polymeric light emitting diodes, photovoltaic cells and field effect transistors. Preferably, such films are used as emitting layers or charge carrier transport layers. The films may also be used as protective coatings for electronic devices and as fluorescent coatings. The thickness of the film or coating is dependent upon the use.

Generally, such thickness can be from 0.005 to 200 microns. When the coating is used as a fluorescent coating, the coating or film thickness is from 50 to 200 microns. When the coatings are used as electronic protective layers, the thickness of the coating can be from 5 to 20 microns. When the coatings are used in a polymeric light-emitting diode, the thickness of the layer formed is 0.005 to 0.2 microns. The polymers of the invention form good pinhole-free and defect-free films.

The films are readily formed by coating the polymer composition in which the composition comprises the polymer and at least one organic solvent. Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6-fluorotoluene, 2-fluoroanisole, anisole, 2,3-dimethylpyrazine, 4-fluoroanisole, 3-fluoroanisole, 3-trifluoromethylanisole, 2-methylanisole, phenetole, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, dioxane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. It is preferable that such solvents have relatively low polarity. High boilers and solvent mixtures are better for ink jetting, but xylenes and toluene are best for spin coating. Preferably, the solution contains from about 0.1 to 5 percent of a polymer comprising a repeat unit of Formula I. Films can be prepared by means well known in the art including spin-coating, spray-coating, dip-coating, roll-coating, offset printing, ink jet printing, screen printing, stamp-coating or doctor blading.

In another embodiment, the invention is a composition comprising a polymer or polymer blend of the invention in a solvent. Solvents which can be used include toluene, xylene, a mixture of o, m and p-isomers of xylene, mesitylene, diethylbenzene, ethylbenzene or benzene derivatives of higher substituted level. Preferably, the solution contains from 0.1 to 10 weight percent of the composition. For thin coatings, it is preferred that the composition contains from 0.5 to 5.0 percent by weight of the composition. The composition is applied to the appropriate substrate by the desired method and the solvent is allowed to evaporate. Residual solvent may be removed by vacuum, heat and/or by sweeping with an inert gas such as nitrogen.

The polymers of this invention demonstrate strong electroluminesence in addition to photoluminesence. Thus, another aspect of the invention relates to organic electroluminescent (EL) devices having a film comprising the polymers of this invention. EL devices based on the polymers of this invention demonstrate improved efficiency over devices in which the electroluminescent polymer film does not contain a repeat unit comprising a tricyclic amine. What we mean is that incorporating a triarylamine moiety in general and a tricyclic amine in particular into the polymers of the instant invention enhances the EL device performance. Preferably, the EL devices of this invention emit light when subjected to an applied voltage of 20 volts or less, 10 volts or less or preferably 6 volts or less.

An organic EL device typically consists of an organic film sandwiched between an anode and a cathode. When a positive bias is applied to the device, holes are injected into the organic film from the anode, and electrons are injected into the organic film from the cathode. The combination of a hole and an electron may give rise to an exciton that may undergo radiative decay to the ground state by liberating a photon.

In practice, the anode is commonly a mixed oxide of tin and indium for its conductivity and transparency. The mixed oxide (ITO) is deposited on a transparent substrate such as glass or plastic so that the light emitted by the organic film may be observed. The organic film may be the composite of several individual layers each designed for a distinct function. Because holes are injected from the anode, the layer next to the anode has the ability of transporting holes. Similarly, the layer next to the cathode has the ability of transporting electrons. In many instances, the electron or hole transporting layer may also act as the emitting layer. In some instances, a single layer may perform the combined functions of hole and electron transport and light emission.

The metallic cathode may be deposited either by thermal evaporation or by sputtering. The thickness of the cathode may be from 1 nm to 1000 nm. The preferred metals are calcium, magnesium, indium, aluminum and barium. A thin layer (1-10 nm) of an alkali or alkaline metal halide, e.g., LiF, NaF, CsF or RbF, may be used as a buffering layer between the light emitting polymer and the cathode, calcium, barium, or magnesium. Alloys of these metals may also be used. Alloys of aluminum containing 1 to 5 percent of lithium and alloys of magnesium containing at least 80 percent of magnesium are preferred.

In a preferred embodiment, the electroluminescent device comprises at least one hole injecting polymer film (PEDOT film, for example) and a light-emitting polymer film comprised of the composition of the invention, arranged between an anode material and a cathode material such that under an applied voltage, holes are injected from the anode material into the light emitting polymer via the hole-injecting polymer film and electrons are injected from the cathode material into the light-emitting polymer film when the device is forward biased, resulting in light emission from the light-emitting layer. In another preferred embodiment, layers of hole-transporting polymers are arranged so that the layer closest to the anode has the lowest oxidation potential, with the adjacent layers having progressively higher oxidation potentials. By these methods, electroluminescent devices having relatively high light output per unit voltage may be prepared.

"Photocells" means a class of optoelectronic devices that can convert incident light energy into electrical energy. Examples of photocells are photovoltaic devices, solar cells, photodiodes, and photodetectors. A photocell generally comprises a transparent or semi-transparent first electrode deposited on a transparent substrate. A polymer film is then formed onto the first electrode that is, in turn, coated by a second electrode. Incident light transmitted through the substrate and the first electrode is converted by the polymer film into excitons that can dissociate into electrons and holes under the appropriate circumstances, thus, generating an electric current.

Another embodiment of the invention relates to metal-insulator-semiconductor field effect transistors comprising one or more of the polymers of the invention which serve as a semiconducting polymer. A field effect transistor comprises five elements. The first element is an insulator layer. The insulator layer is an electrical insulator, having a first side and a second side. The second element is a gate. The gate is an electrical conductor. The gate is positioned adjacent to the first side of the insulator layer.

The third element is a semiconductor layer. The semiconductor layer comprises a polymer comprising a structure unit of Formula II above. The semiconductor layer has a first side, a second side, a first end and a second end, the second side of the semiconductor layer being adjacent to the second side of the insulator layer. The polymer is deposited onto an insulator wherein the polymers are present as single-layer films or as multiple-layer films whose combined thickness is in the range of 10 nm to 1000 nm, preferably in the range of 25 nm to 500 nm, most preferably in the range of 50 nm to 300 nm.

The fourth element of a field effect transistor is a source. The source is an electrical conductor. The source is in electrical contact with the first end of the semiconductor layer. The fifth element is a drain. The drain is an electrical conductor. The drain is in electrical contact with the second end of the semiconductor layer. A negative voltage bias applied to the gate causes the formation of a hole conduction channel in the semiconductor layer connecting the source to the drain. A positive bias applied to the gate causes the formation of an electron-conducting channel in the semiconductor layer.

As with electroluminescent devices, the polymer films comprising the semiconductor layer may be formed by solvent-based processing techniques such as spin-coating, roller-coating, dip-coating, spray-coating and doctor-blading and ink jet printing. When two or more polymers are used, they may be deposited separately as distinct layers or deposited as one layer from a solution containing a blend of the desired polymers.

Two electrodes (source and drain) are attached to the semi-conducting polymer and a third electrode (gate) onto the opposite surface of the insulator. If the semiconducting polymer is hole transporting (i.e, the majority carriers are positive holes), then applying a negative DC voltage to the gate electrode induces an accumulation of holes near the polymer-insulator interface, creating a conduction channel through which electric current can flow between the source and the drain. The transistor is in the "on" state. Reversing the gate voltage causes a depletion of holes in the accumulation zone and cessation of current. The transistor is in the "off" state.

The following examples detail the preparation of specific preferred polymers of the instant invention for use, for example and without limitation thereto, in a light emitting diode device and a comparative example.

The following example details the preparation of a specific preferred compound.

EXAMPLE 1

Synthesis of monomer, fluorene-bis-salicylate or 2,7-dibromo-9,9-bis(4-hexyloxy-3-ethoxycarbonylphenyl)fluorene (2) (Scheme 1)

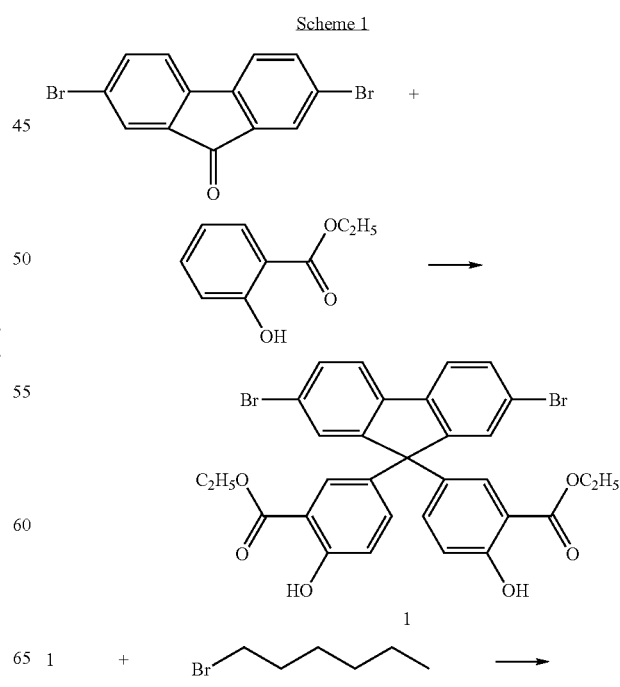

-continued

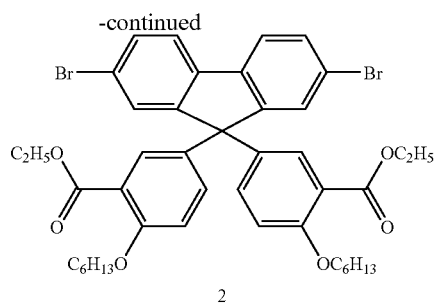

2

A mixture of 2,7-dibromo-9-fluorenone (20.28 g, 60 mmol), ethyl salicylate (59.82 g 360 mmol), mercaptoacetic acid (0.55 g, 6 mmol) and methanesulfonic acid (250 mL) is stirred at 75 degrees Celsius under nitrogen overnight. The mixture is cooled to ambient temperature, and then gradually added to a beaker with ice/water. The resulting mixture is stirred for 1 hour. An orange solid is precipitated. The solid is washed with hot acetonitrile. The crude product is re-crystallized from acetone yielding 22.2 g of product (1) as a light orange solid having a purity of about 97%. Proton NMR is used to confirm the structure. 3.26 g of (1) (5 mmol), 2.48 g of 1-bromohexane (15 mmol), 3.46 g of potassium carbonate (25 mmol), 0.4 g of 18-crown-6 (1.5 mmol) and 35 milliliters of DMF are charged to a round bottom flask equipped with a magnetic stirring bar. The mixture is stirred at 105 degrees Centigrade overnight. The mixture is cooled to ambient temperature, and then gradually added to a beaker with ice/water. The resulting mixture is stirred for 1 hour. A solid is precipitated. The product is re-crystallized from EtOH yielding 2.6 g of 2,7-dibromo-9,9-bis(4-hexyloxy-3-ethoxycarbonylphenyl)fluorene (2) as a pale yellow solid having a purity of about 97%. Proton NMR and mass spectroscopy are used to confirm the structure (2).

COMPARATIVE EXAMPLE 2

Polymer 1

Polymerization procedure for Polymer 1-Blue Light Emitting Polymer

Into a 250 mL three-necked flask equipped with an overhead stirrer and a condenser is placed 9,9-dioctylfluorene-2,7-boronic acid ethylene glycol ester (99.9%, 3.206 g, 6.038 mmol), 2,7-dibromo-9,9-di(4'-ethoxyethoxyphenyl)fluorene (99.5%, 2.940 g, 4.483 mmol), 3,7-dibromo-N-(4-n-butylphenyl)-phenoxazine (99.9%, 0.7079 g, 1.494 mmol), toluene (50 mL), phase transfer reagent, Aliquat 336 (0.87 g), trans-dichlorobis-(triphenylphosphine)-palladium(II) (4.2 mg), and 2M aqueous sodium carbonate solution (13 mL). The system is purged with nitrogen. The mixture is gently refluxed at 105 degrees Celsius until a viscous mixture is observed. To terminate the polymerization, 0.2 g phenyl boronic acid in THF and 10 mL toluene are added. The mixture is refluxed for 6 hours. An aqueous solution of sodium diethyldithiocarbamate trihydrate (DDC, 3.5 g in 35 mL of water) is added. The mixture is stirred under nitrogen at about 88 degrees Celsius overnight. The viscous mixture is transferred to a separatory funnel and the aqueous layer is removed. The organic phase is washed twice with 2% acetic acid (aq) and three times with warm distilled water, passed through a column of Celite/silica gel/basic alumina using toluene as the eluent. The diluted polymer solution is concentrated on a rotary evaporator to a 2% by weight solution. The polymer is precipitated by adding methanol and then dried under vacuum at 55 degrees Celsius. The crude polymer is re-dissolved in toluene (CMOS grade) with heating and precipitated a second time by adding methanol (CMOS grade). The polymer is filtered, washed with methanol (CMOS grade) and dried in a vacuum oven at 55 degrees Celsius. 3.6 grams of polymer are obtained having a Mw of 570,000 grams per mole and a polydispersity index of 2.9.

EXAMPLE 3

Polymer 2

Polymerization procedure for Polymer 2-Blue Light Emitting Polymer

This procedure of this example is similar to that of Example 2. Monomers and reagents used for the polymerization are listed as follows: 9,9-dioctylfluorene-2,7-boronic acid ethylene glycol ester (99.9%, 2.385 g, 4.491 mmol), 2,7-dibromo-9,9-di(4'-ethoxyethoxyphenyl)fluorene (99.5%, 1.094 g, 1.668 mmol), 2,7-dibromo-9,9-bis(4-hexyloxy-3-ethoxycarbonylphenyl)fluorene, 2, (99.5%, 1.376 g, 1.668 mmol), 3,7-dibromo-N-(4-n-butylphenyl)phenoxazine (99.9%, 0.527 g, 1.111 mmol), toluene (40 mL), phase transfer reagent, Aliquat 336 (0.66 g), trans-dichlorobis-(triphenylphosphine)-palladium(II) (3.1 mg), and 2M aqueous sodium carbonate solution (10 mL). 2.9 g of polymer are obtained having a Mw of 230,000 grams per mole and a polydispersity index of 2.3.

EXAMPLE 4

Polymer 3

Polymerization procedure for Polymer 3-Blue Light Emitting Polymer

This procedure of this example is similar to that of Example 2. Monomers and reagents used for the polymerization are listed as follows: 9,9-dioctylfluorene-2,7-boronic acid ethylene glycol ester (99.9%, 2.442 g, 4.599 mmol), 2,7-dibromo-9,9-di(4'-ethoxyethoxyphenyl)fluorene (99.6%, 1.491 g, 2.277 mmol), 2,7-dibromo-9,9-bis(4-hexyloxy-3-ethoxycarbonylphenyl)fluorene, 2, (99.7%, 0.937 g, 1.138 mmol), 3,7-dibromo-N-(4-n-butylphenyl)phenoxazine (99.9%, 0.539 g, 1.138 mmol), toluene (40 mL), phase transfer reagent, Aliquat 336 (0.65 g), trans-dichlorobis-(triphenylphosphine)-palladium(II) (3.0 mg), and 2M aqueous sodium carbonate solution (10 mL). 2.7 g of polymer are obtained having a Mw of 290,000 grams per mole and a polydispersity index of 2.3.

EXAMPLE 5

Polymer 4

Polymerization procedure for Polymer 4-Blue Light Emitting Polymer

This procedure of this example is similar to that of Example 2. Monomers and reagents used for the polymerization are listed as follows: 9,9-dioctylfluorene-2,7-boronic acid ethylene glycol ester (99.9%, 2.489 g, 4.689 mmol), 2,7-dibromo-9,9-di(4'-ethoxyethoxyphenyl)fluorene (99.6%, 1.824 g, 2.785 mmol), 2,7-dibromo-9,9-bis(4-hexyloxy-3-ethoxycarbonylphenyl)fluorene, 2, (99.7%, 0.573 g, 0.696 mmol), 3,7-dibromo-N-(4-n-butylphenyl)-phenoxazine (99.9%, 0.550 g, 1.161 mmol), toluene (40 mL), phase transfer reagent, Aliquat 336 (0.68 g), trans-dichlorobis-(triphenylphosphine)-palladium(II) (3.6 mg), and 2M aqueous sodium carbonate solution (10 mL). 2.9 g of polymer is obtained having a Mw of 339,000 grams per mole and a polydispersity index of 2.5.

EXAMPLE 6

(Polymer 5) Polymerization Procedure for Polymer 5-Blue Light Emitting Polymer

Into a 250 mL three-necked flask equipped with an overhead stirrer and a condenser was placed 9,9-dioctylfluorene-2,7-boronic acid ethylene glycol ester (F8-BE) (99.9%, 2.229 g, 4.197 mmol), 2,7-dibromo-9,9-bis(4-hexyloxy-3-ethoxycarbonylphenyl)fluorene (BSAFBr$_2$) (99.7%, 2.565 g, 3.117 mmol), 3,7-dibromo-N-(4-n-butylphenyl)phenoxazine (POZBr$_2$) (99.9%, 0.492 g, 1.039 mmol), toluene (40 mL), phase transfer reagent, Aliquat 336 (0.60 g), trans-dichlorobis (triphenylphosphine)-palladium(II) (2.9 mg), and 2M aqueous sodium carbonate solution (9 mL). The system was purged with nitrogen. The mixture was gently refluxed (105° C.) for ~2.5 hours until a viscous mixture was observed. To terminate the polymerization, 0.2 g phenyl boronic acid in THF and 10 mL toluene were added. The mixture was refluxed for 5 hours. An aqueous solution of sodium diethyldithiocarbamate trihydrate (DDC, 3.5 g in 35 mL of water) was added. The mixture was stirred under nitrogen at ~88° C. overnight. The mixture was transferred to a separatory funnel and the aqueous layer was removed. The organic phase was washed with 2% acetic acid (aq) and warm distilled water, passed through a column of Celite/silica gel/basic alumina, and eluted with toluene. The diluted polymer solution was concentrated on a rotary evaporator to a ~1-2% by weight solution. The polymer was precipitated from methanol and dried under vacuum at 55° C. The crude polymer was re-dissolved in toluene (CMOS grade) with heating and precipitated a second time from methanol (CMOS grade). The polymer was filtered, washed with methanol (CMOS grade) and dried in a vacuum oven at 55° C. overnight. 2.8 g (70%) of polymer was obtained: Mw=370,000; PDI (polydispersity index)=2.2. DSC measurement shows that this polymer is an amorphous polymer with a glass transition temperature (T$_g$) of 135° C.

The data in the above table show the significantly improved lifetimes for the devices made from polymers of the instant invention (Polymers 2-4) compared to the prior art polymer (Polymer 1). Thus, without wishing to be bound by theory, Applicants believe that the salicylate group of the instant invention complexes to the cathode metal in its cationic state leading to enhanced electron injection from the cathode, thereby, promoting the surprising improvement in device efficiency and lifetime.

Conclusion

While this invention has been described as having preferred aspects, the instant invention can be further modified within the spirit and scope of this disclosure. This application is, therefore, intended to cover any variations, uses, or adaptations of the present invention using the general principles disclosed herein. Further, this application is intended to cover such departures from the present disclosure as come within the known or customary practice in the art to which this invention pertains and which fall within the limits of the appended claims.

What is claimed is:
1. A compound of Formula (I):

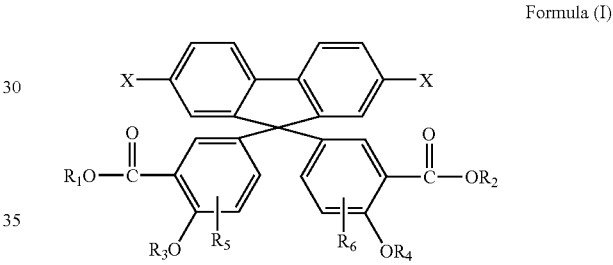

Formula (I)

wherein R$_1$, R$_2$, R$_3$, R$_4$ are the same or different and each is independently H, alkyl in which one or more C and/or H may be substituted with at least one of O, N, S, Si, P and F, aralkyl, aryl, substituted aryl, heteroaryl, substituted heteroaryl; X is halogen, boronic acid or boronate ester; and R$_0$ and R$_6$ are the same or different and each is independently in each occurrence hydrogen, C$_{1-20}$ hydrocarbyl, C$_{1-20}$ hydrocarbyloxy, C$_{1-20}$ thioether, C$_{1-20}$ hydrocarbyloxycarbonyl, C$_{1-20}$ hydrocarbylcarbonyloxy, cyano, or fluoro.

| | Comparison of Polymers 1-5 in a light emitting diode device | | | | | | |
|---|---|---|---|---|---|---|---|
| Polymer | Light Efficiency (Cd/A) @ 200 Cd/m$^2$ | Light Efficiency (Cd/A) @ 1000 Cd/m$^2$ | Light Efficiency (Cd/A) @ 4000 Cd/m$^2$ | Light Efficiency (Cd/A) @ 10000 Cd/m$^2$ | Max Brightness (Cd/m$^2$) | Color Coordinates CIE (1931) (X, Y) | AC Life time (hours) |
| Polymer 1 | 3.55 | 4.39 | 4.87 | 4.84 | 13489 | 0.15, 0.26 | 396 |
| Polymer 2 | 3.14 | 3.81 | 4.01 | 3.85 | 9241 | 0.17, 0.27 | 472 |
| Polymer 3 | 3.68 | 4.33 | 4.60 | 4.37 | 10992 | 0.15, 0.26 | 469 |
| Polymer 4 | 3.71 | 4.45 | 4.79 | 4.70 | 13018 | 0.15, 0.25 | 439 |
| Polymer 5 | 4.4 | 4.5 | 4.1 | N/A | 4404 | 0.15, 0.27 | 508 |

2. A polymer comprising a structural unit of Formula (II):

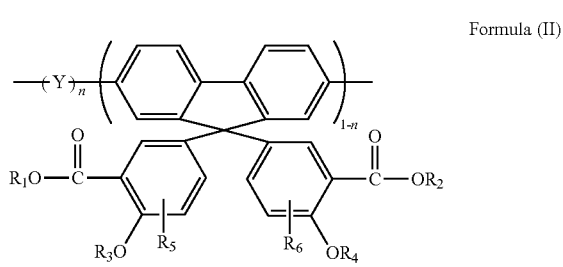

Formula (II)

wherein $R_1$, $R_2$, $R_3$, $R_4$ are the same or different and each is independently H, alkyl in which one or more C and/or H may be substituted with at least one of O, N, S, Si, P and F, aralkyl, aryl, substituted aryl, heteroaryl, and substituted heteroaryl; and Y is a conjugated unit; and $R_5$ and $R_6$ are the same or different and each is independently in each occurrence hydrogen, $C_{1-20}$ hydrocarbyl, $C_{1-20}$ hydrocarbyloxy, $C_{1-20}$ thioether, $C_{1-20}$ hydrocarbyloxycarbonyl, $C_{1-20}$ hydrocarbylcarbonyloxy, cyano, or fluoro, wherein n is a real number ranging from at or between 0 and 0.999.

3. The polymer of claim 2, wherein n is zero.

4. The polymer of claim 2, wherein Y is one or more of the following:

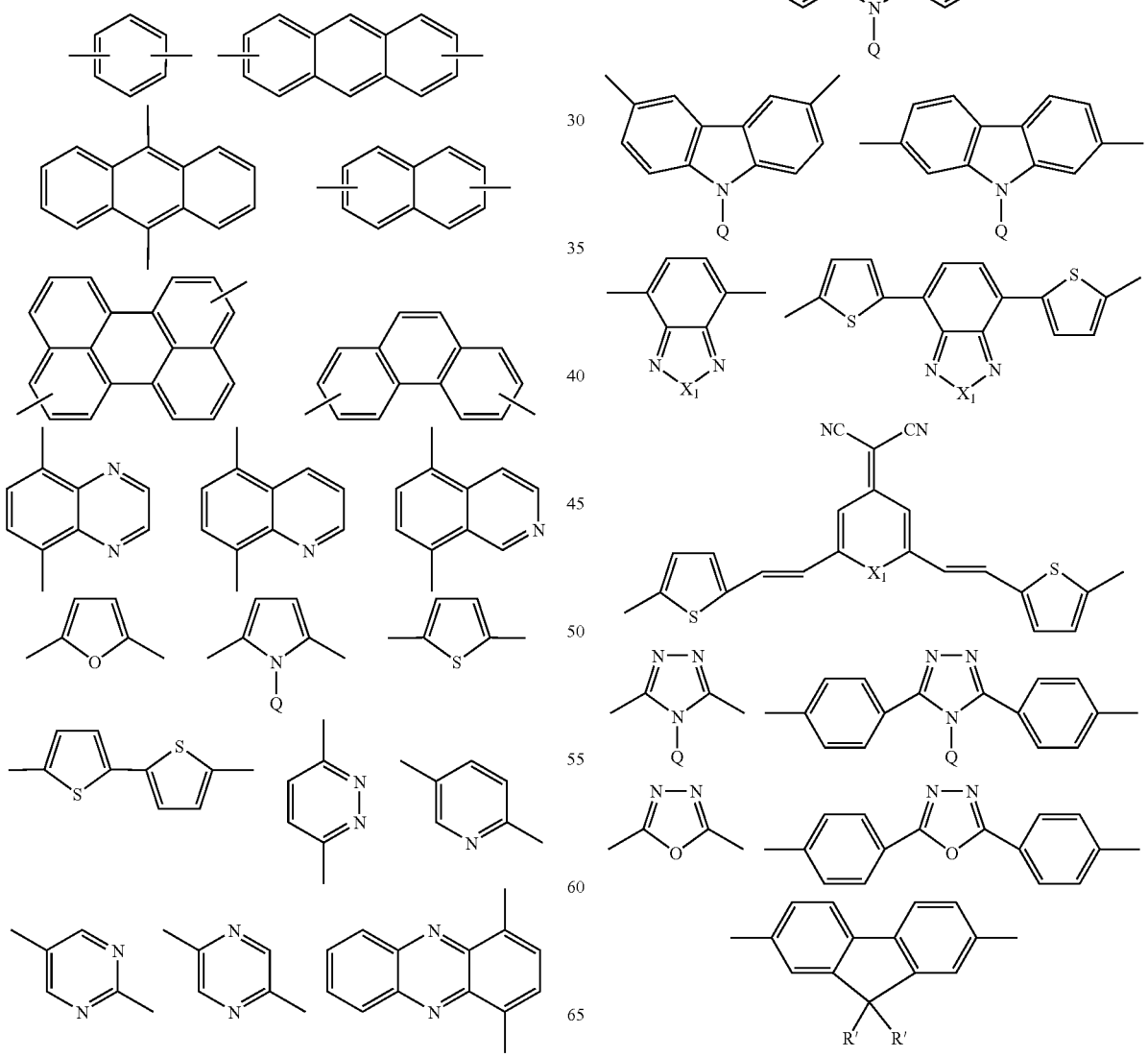

-continued

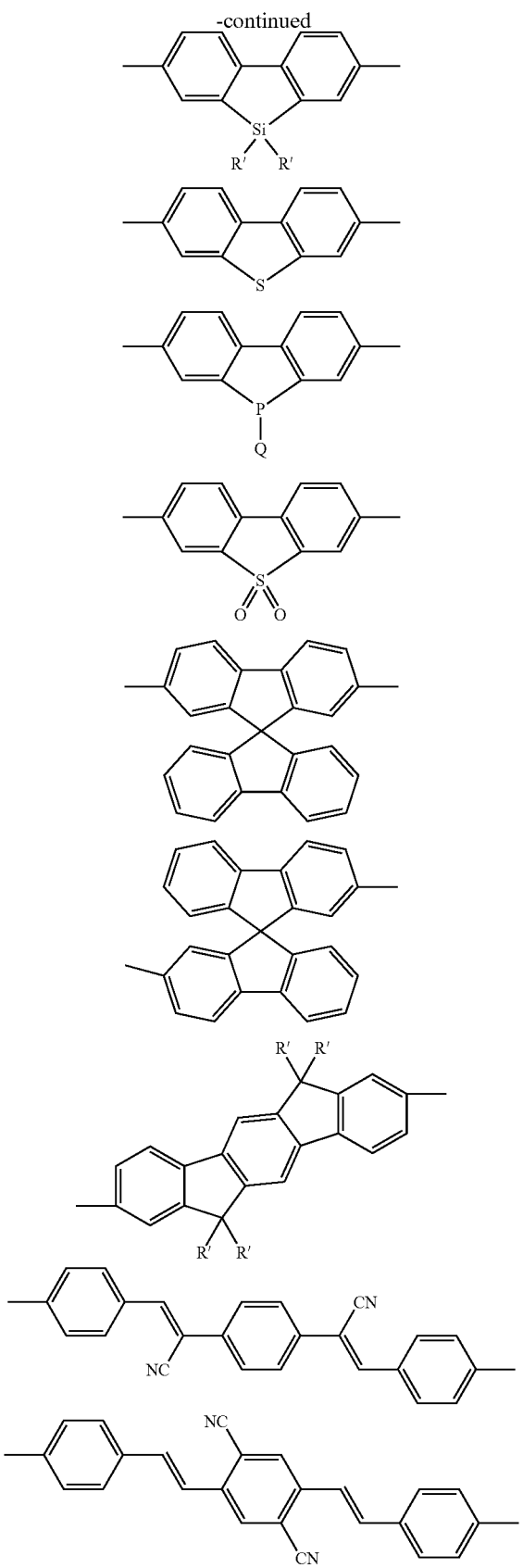

-continued

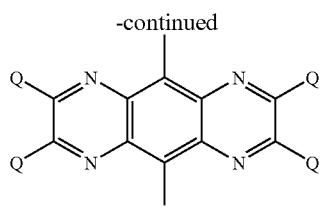

wherein the conjugated units may have substituents, the substituent being independently in each occurrence $C_{1-20}$ hydrocarbyl, $C_{1-20}$ hydrocarboxyloxy, $C_{1-20}$ thioether, $C_{1-20}$ hydrocarbyloxycarbonyl, $C_{1-20}$ hydrocarboxy carbonyloxy, cyano, or fluoro group;

$X_1$ is O or S;

Q is R or Ar;

R is $C_{1-40}$ hydrocarbyl or $C_{3-40}$ hydrocarbyl containing one or more S, N, O, P or Si atoms, cyano or fluoro;

Ar is an aryl or heteroaryl group of $C_4$ to $C_{40}$ or substituted aryl or heteroaryl group of $C_4$ to $C_{40}$;

R' is independently, in each occurrence H, $C_{1-40}$ hydrocarbyl or $C_{3-40}$ hydrocarbyl containing one or more S, N, O, P or Si atoms, or both of R' together with the 9-carbon on the fluorene may form a $C_{5-20}$ ring structure which may contain one or more S, N, or O atoms.

5. A composition comprising the polymer of claim 2.

6. An electronic device selected from the group consisting of electroluminescence devices, photocells and field effect transistors comprising a film or coating comprising the polymer of claim 2.

7. An oligomer comprising Formula (II):

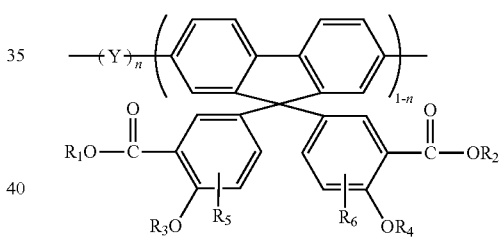

Formula (II)

wherein $R_1$, $R_2$, $R_3$, $R_4$ are the same or different and each is independently H, alkyl in which one or more C and/or H may be substituted by at least one of O, N, S, Si, P and F, aralkyl, aryl, substituted aryl, heteroaryl, and substituted heteroaryl; Y is a conjugated unit; and $R_5$ and $R_6$ are the same or different and each is independently in each occurrence hydrogen, $C_{1-20}$ hydrocarbyl, $C_{1-20}$ hydrocarbyloxy, $C_{1-20}$ thioether, hydrocarbyloxycarbonyl, $C_{1-20}$ hydrocarbylcarbonyloxy, cyano, or fluoro, wherein n is a real number ranging from at or between 0 and 0.999.

8. The polymer of claim 2, wherein the polymer is conjugated or partially conjugated.

9. The polymer of claim 2, wherein the polymer is linear, branched, hyperbranched, homopolymer, alternating copolymer, random copolymer, block copolymer or grated copolymer.

10. The composition of claim 5, further comprising a solvent, an oligomer, or a polymer.

11. A polymer blend comprising the polymer of claim 2.

12. A film comprising the polymer of claim 2.

* * * * *